United States Patent
Daw et al.

(10) Patent No.: US 9,960,341 B1
(45) Date of Patent: May 1, 2018

(54) HIGH FREQUENCY MAGNETOSTRICTIVE TRANSDUCERS FOR WAVEGUIDE APPLICATIONS

(71) Applicants: Joshua Earl Daw, Idaho Falls, ID (US); Steven Cheney Taylor, Ammon, ID (US); Joy Lynn Rempe, Idaho Falls, ID (US)

(72) Inventors: Joshua Earl Daw, Idaho Falls, ID (US); Steven Cheney Taylor, Ammon, ID (US); Joy Lynn Rempe, Idaho Falls, ID (US)

(73) Assignee: U.S. Department of Energy, Washington, DC (US)

( * ) Notice: Subject to any disclaimer, the term of this patent is extended or adjusted under 35 U.S.C. 154(b) by 628 days.

(21) Appl. No.: 14/554,159

(22) Filed: Nov. 26, 2014

(51) Int. Cl.
H01L 27/20 (2006.01)
H01L 41/12 (2006.01)

(52) U.S. Cl.
CPC .............. *H01L 41/12* (2013.01); *H01L 27/20* (2013.01)

(58) Field of Classification Search
CPC ......... H01L 41/00; H04R 15/00; H04R 15/02; H02N 2/00; G01L 1/125; B06B 2201/58
USPC .............................................. 310/26; 318/118
See application file for complete search history.

(56) References Cited

U.S. PATENT DOCUMENTS

| | | | | |
|---|---|---|---|---|
| 2,612,603 A | * | 9/1952 | Nicholson, Jr. ....... | G01S 7/2926 310/26 |
| 3,046,501 A | * | 7/1962 | Dell ...................... | H03H 9/125 310/26 |
| 3,369,135 A | * | 2/1968 | Hotine ................... | G04C 3/125 310/21 |
| 4,017,754 A | * | 4/1977 | Jarrett .................... | H01L 41/12 310/26 |
| 4,151,432 A | * | 4/1979 | Akimoto ................. | B06B 1/08 264/DIG. 58 |
| 4,413,892 A | * | 11/1983 | Lambeth ................ | G01D 5/485 324/207.13 |
| 4,514,688 A | * | 4/1985 | Whetstone ............. | G01B 7/004 178/18.02 |
| 5,184,037 A | * | 2/1993 | Kobayashi ............. | H01L 41/12 310/26 |
| 5,412,316 A | * | 5/1995 | Dumais .................. | G01B 7/02 324/207.13 |

(Continued)

FOREIGN PATENT DOCUMENTS

| | | | | | |
|---|---|---|---|---|---|
| GB | | 405620 A | * | 1/1934 | .............. B06B 1/08 |
| JP | 2007158911 A | * | 6/2007 | | |

*Primary Examiner* — Quyen Leung
*Assistant Examiner* — Eric Johnson
(74) *Attorney, Agent, or Firm* — Felisa L. Leisinger; Michael J. Dobbs; Brian J. Lally (57) ABSTRACT

A high frequency magnetostrictive transducer includes a magnetostrictive rod or wire inserted co-axially into a driving coil, wherein the driving coil includes a coil arrangement with a plurality of small coil segments along the magnetostrictive rod or wire; wherein frequency operation of the high frequency magnetostrictive transducer is controlled by a length of the small coil segments and a material type of the magnetostrictive rod or wire. This design of the high frequency magnetostrictive transducer retains the beneficial aspects of the magnetostrictive design, while reducing its primary drawback, lower frequency operation.

18 Claims, 9 Drawing Sheets

(56) References Cited

U.S. PATENT DOCUMENTS

| | | | | |
|---|---|---|---|---|
| 5,989,202 | A * | 11/1999 | Noda | B06B 3/00 310/26 |
| 7,675,253 | B2 * | 3/2010 | Dorel | E21B 34/066 166/65.1 |
| 8,093,869 | B1 * | 1/2012 | Gunderson | H02K 35/06 310/26 |
| 2007/0011836 | A1 * | 1/2007 | Brewer | A46B 15/0002 15/220.1 |

* cited by examiner

NO MAGNETIC FIELD

HIGH FREQUENCY MAGNETOSTRICTIVE TRANSDUCERS FOR WAVEGUIDE APPLICATIONS

STATEMENT REGARDING FEDERALLY SPONSORED RESEARCH OR DEVELOPMENT

The United States Government has rights in this invention pursuant to Contract No. DE-AC07-05ID14517, between the U.S. Department of Energy (DOE) and Battelle Energy Alliance (BEA), representing Idaho National Laboratory (INL).

FIELD OF THE DISCLOSURE

The present disclosure relates generally to magnetostrictive transducers. More particularly, the present disclosure relates to high frequency magnetostrictive transducers for thin wire waveguide applications.

BACKGROUND OF THE DISCLOSURE

Ultrasonic transducers are used to generate high frequency sound waves, such as for non-destructive evaluation to scan objects and identify defects and as a core technology of various sensor systems for measuring a wide variety of parameters. Conventionally, transducers are based on piezoelectric crystals (or ceramics) or magnetostrictive alloys. Piezoelectric materials account for nearly all ultrasonic transducers currently in use, as they are small, have high power, have high frequency capability, are a well-developed technology, and operate as capacitive elements (voltage based signal). However, piezoelectric crystals are fragile and can be difficult to acoustically couple to metals. Magnetostrictive transducers are used for various technologies, but are less developed. Magnetostrictive alloys are durable, easy to couple to metals (welding, brazing, soldering); some common structural materials are magnetostrictive (nickel, iron), and operate as inductive elements (current based signal). However, transducers based on magnetostrictive alloys operate at lower frequencies than comparable transducers based on piezoelectric materials. For example, conventional magnetostrictive transducers are typically limited to frequencies below 200 kHz and have a very narrow bandwidth (e.g., a 120 kHz transducer will not operate at 110 kHz or 130 kHz drive frequency). It would be advantageous for higher frequency operation of transducers based on magnetostriction.

BRIEF SUMMARY OF THE DISCLOSURE

In an exemplary embodiment, a high frequency magnetostrictive transducer includes a magnetostrictive rod or wire inserted co-axially into a driving coil, wherein the driving coil includes a coil arrangement with a plurality of small coil segments along the magnetostrictive rod or wire; wherein frequency operation of the high frequency magnetostrictive transducer is controlled by a length of the small coil segments and a material type of the magnetostrictive rod or wire. The frequency operation of the high frequency magnetostrictive transducer has been demonstrated up to a peak center frequency of approximately 2 MHz with 36% bandwidth (3 dB). The operating frequency range of the high frequency magnetostrictive transducer can be between approximately 1 MHz and 3 MHz before signal amplitude drops to 50% and with similar bandwidth to the peak. Each of the small coil segments can be spaced apart from adjacent small coil segments with open space on the magnetostrictive rod or wire therebetween. The plurality of small coil segments can each form a magnetic field orientation that, collectively, constructively interfere with one another, resulting in greater signal strength. Optionally, the plurality of small coil segments can be each wound in a uniform direction. Alternatively, the plurality of small coil segments can be each wound in alternating directions. The plurality of small coil segments allows the magnetostrictive rod or wire to be driven at higher harmonics, resulting in higher frequency operation.

In another exemplary embodiment, a high frequency magnetostrictive transducer method includes inserting a magnetostrictive rod or wire co-axially into a driving coil, wherein the driving coil includes a coil arrangement with a plurality of small coil segments along the magnetostrictive rod or wire; wherein frequency operation of the high frequency magnetostrictive transducer is controlled by a length of the small coil segments and a material type of the magnetostrictive rod or wire. The frequency operation of the high frequency magnetostrictive transducer has been demonstrated up to a peak center frequency of approximately 2 MHz with 36% bandwidth (3 dB). The operating frequency range of the high frequency magnetostrictive transducer can be between approximately 1 MHz and 3 MHz before signal amplitude drops to 50% and with similar bandwidth to the peak. Each of the small coil segments can be spaced apart from adjacent small coil segments with open space on the magnetostrictive rod or wire therebetween. The plurality of small coil segments can each form a magnetic field orientation that, collectively, constructively interfere with one another, resulting in greater signal strength. Optionally, the plurality of small coil segments can be each wound in a uniform direction. Alternatively, the plurality of small coil segments can be each wound in alternating directions. The plurality of small coil segments allows the magnetostrictive rod or wire to be driven at higher harmonics, resulting in higher frequency operation.

In a further exemplary embodiment, a high frequency magnetostrictive transducer system includes one or more high frequency magnetostrictive transducers comprising a magnetostrictive rod or wire inserted co-axially into a driving coil, wherein the driving coil includes a coil arrangement with a plurality of small coil segments along the magnetostrictive rod or wire, and wherein frequency operation of the high frequency magnetostrictive transducer is controlled by a length of the small coil segments and a material type of the magnetostrictive rod or wire; a source configured to drive the one or more high frequency magnetostrictive transducers; and a detection device coupled to the one or more high frequency magnetostrictive transducers. The frequency operation of the high frequency magnetostrictive transducer has been demonstrated up to a peak center frequency of approximately 2 MHz with 36% bandwidth (3 dB). The operating frequency range of the high frequency magnetostrictive transducer can be between approximately 1 MHz and 3 MHz before signal amplitude drops to 50% and with similar bandwidth to the peak. Each of the small coil segments can be spaced apart from adjacent small coil segments with open space on the magnetostrictive rod or wire therebetween. The plurality of small coil segments each form a magnetic field orientation that, collectively, constructively interfere with one another, resulting in greater signal strength.

BRIEF DESCRIPTION OF THE DRAWINGS

The present disclosure is illustrated and described herein with reference to the various drawings, in which like reference numbers are used to denote like system components/ method steps, as appropriate, and in which.

DETAILED DESCRIPTION OF THE DISCLOSURE

In various exemplary embodiments, high frequency magnetostrictive transducers are described for waveguide applications. The high frequency magnetostrictive transducers support higher frequency operation, e.g., such as about 2 MHz compared to 200 kHz for conventional magnetostrictive transducers, and support increased bandwidth, or range of operation, such as between about 1 and 3 MHz compared to less than a 10 kHz range for conventional magnetostrictive transducers.

Figure 1:
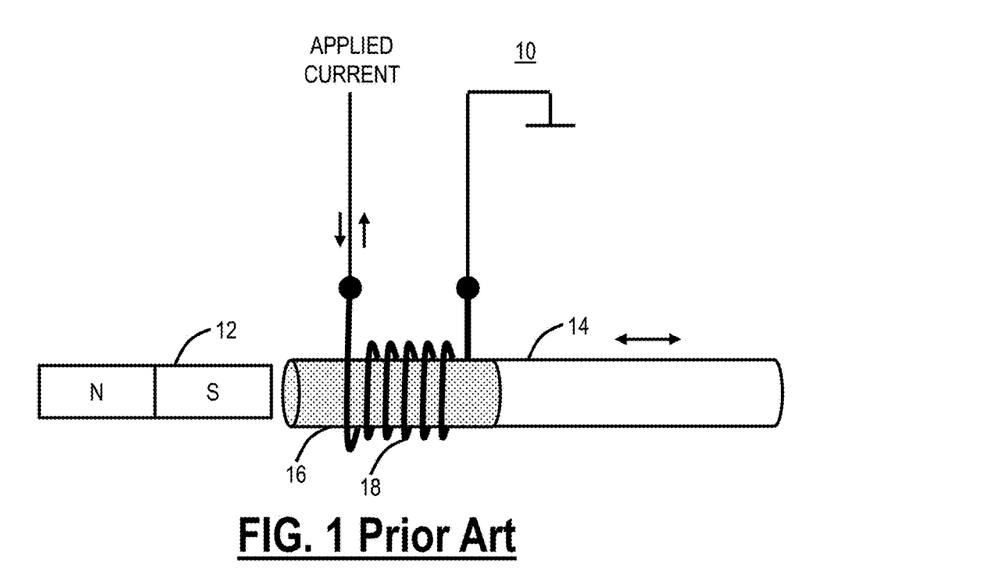
FIG. 1 is a block diagram of a magnetostrictive transducer for ultrasonic applications in a conventional embodiment.

Referring to FIG. 1, in a conventional embodiment, a block diagram illustrates a magnetostrictive transducer 10 for ultrasonic waveguide applications. The magnetostrictive transducer 10 includes a polarizing magnet 12 located near a waveguide 14. The waveguide 14 includes a magnetostrictive stub portion 16 which includes an excitation coil 18 tightly wrapped around the magnetostrictive stub portion 16. In operation, a current is applied through the excitation coil 18 causing the magnetostrictive stub portion 16 to transduce or convert magnetic energy to mechanical energy and vice versa. As the magnetostrictive stub portion 16 is magnetized, it strains; that is, it exhibits a change in length per unit length. Stated differently, when a flow of electrical current is supplied through the excitation coil 18, a magnetic field is created and causes the magnetostrictive stub portion 16 to contract or elongate, thereby creating a sound wave.

Figure 2:
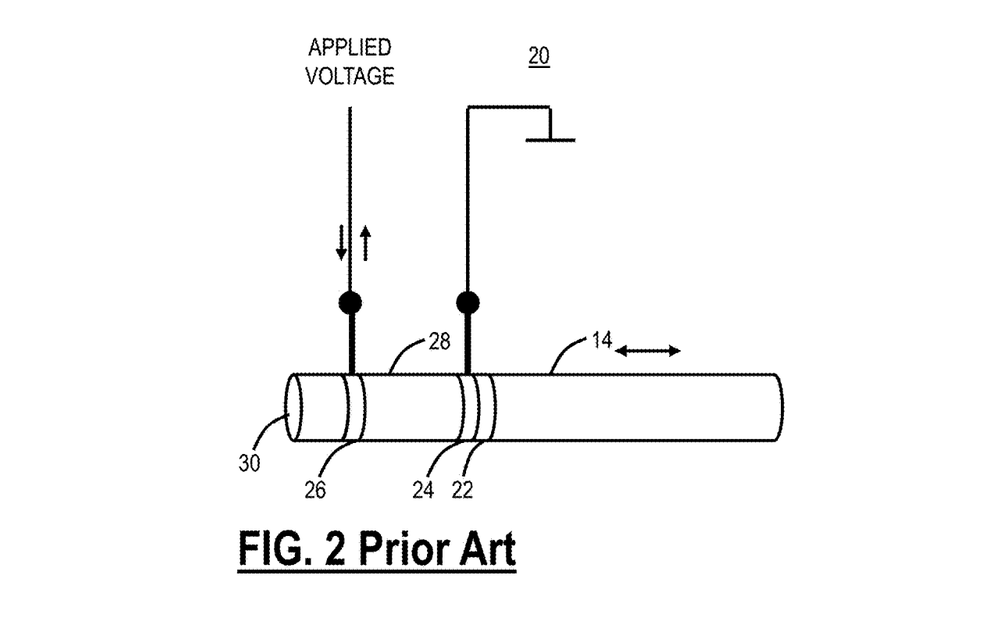
FIG. 2 is a block diagram of a piezoelectric transducer for ultrasonic applications in a conventional embodiment.

Referring to FIG. 2, in a conventional embodiment, a block diagram illustrates a piezoelectric transducer 20 for ultrasonic waveguide applications. The piezoelectric transducer 20 includes a waveguide 14, an impedance matching layer 22, electrodes 24, 26, a piezoelectric element 28, and a backing material 30. A voltage is applied between the electrodes 24, 26 through the piezoelectric element 28 causing mechanical vibrations. Typical ultrasonic frequencies range from 20 kHz into the GHz range. Due to physical size limitations of the magnetostrictive transducer 10 (frequency is dependent on the length of the transducer with higher frequency requiring a shorter and shorter length) it is typically limited to operate at frequencies below approximately 200 kHz. The piezoelectric transducer 20 is not frequency limited within this range. However, the piezoelectric transducer 20 is fragile and difficult to couple to metals.

Figure 3:
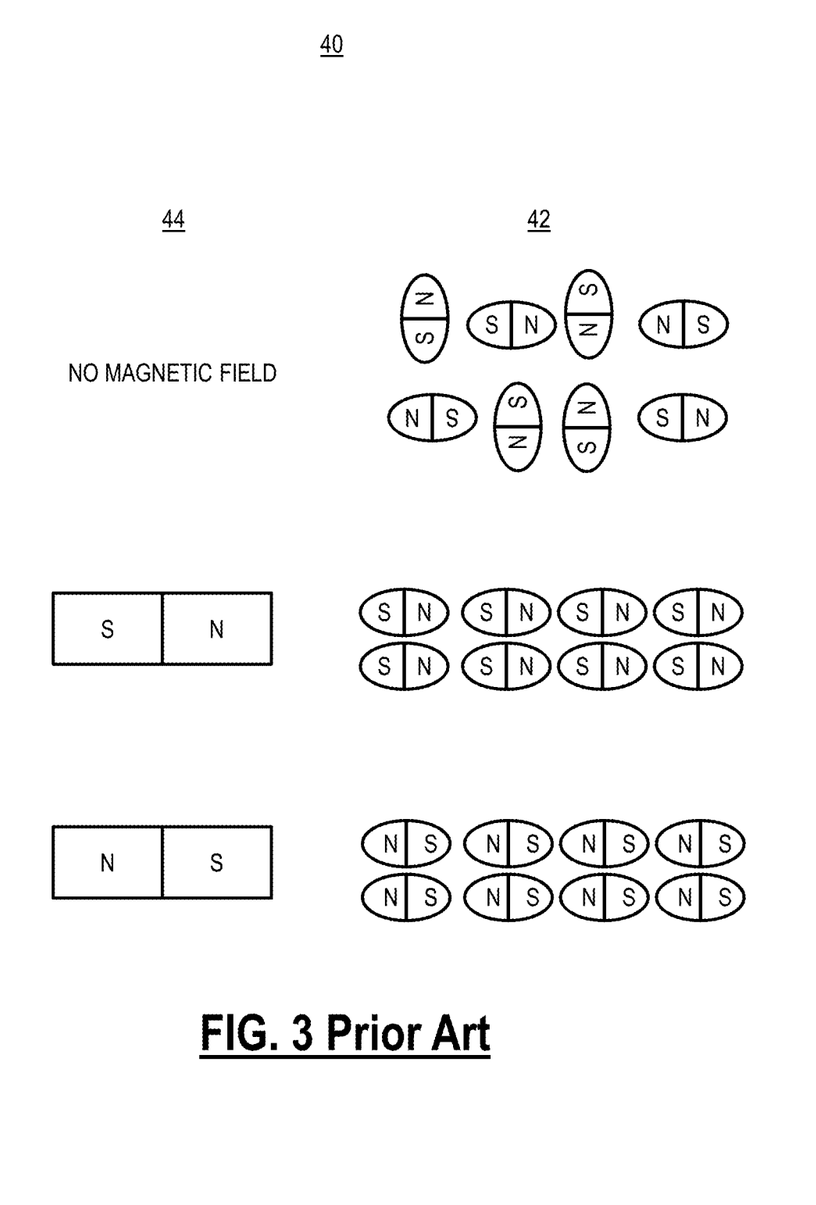
FIG. 3 is a block diagram of the magnetostrictive effect as used in the magnetostrictive transducer of FIG. 1.

Referring to FIG. 3, in a conventional embodiment, a block diagram illustrates the magnetostrictive effect 40 as used in the magnetostrictive transducer 10. Specifically, FIG. 3 illustrates a ferromagnetic material 42 in the presence or absence of an alternating magnetic field 44. Magnetostriction is a property of the ferromagnetic material 42 that causes it to change their shape or dimensions during the process of magnetization. The variation of the ferromagnetic material's 42 magnetization due to the applied magnetic field changes the magnetostrictive strain until reaching its saturation value, $\lambda$. Magnetostrictive materials can convert magnetic energy into kinetic energy, or the reverse, and are used to build actuators and sensors. The property can be quantified by the magnetostrictive coefficient, $\Lambda$, which may be positive or negative and is defined as the fractional change in length as the magnetization of the material increases from zero to the saturation value.

Figure 4:
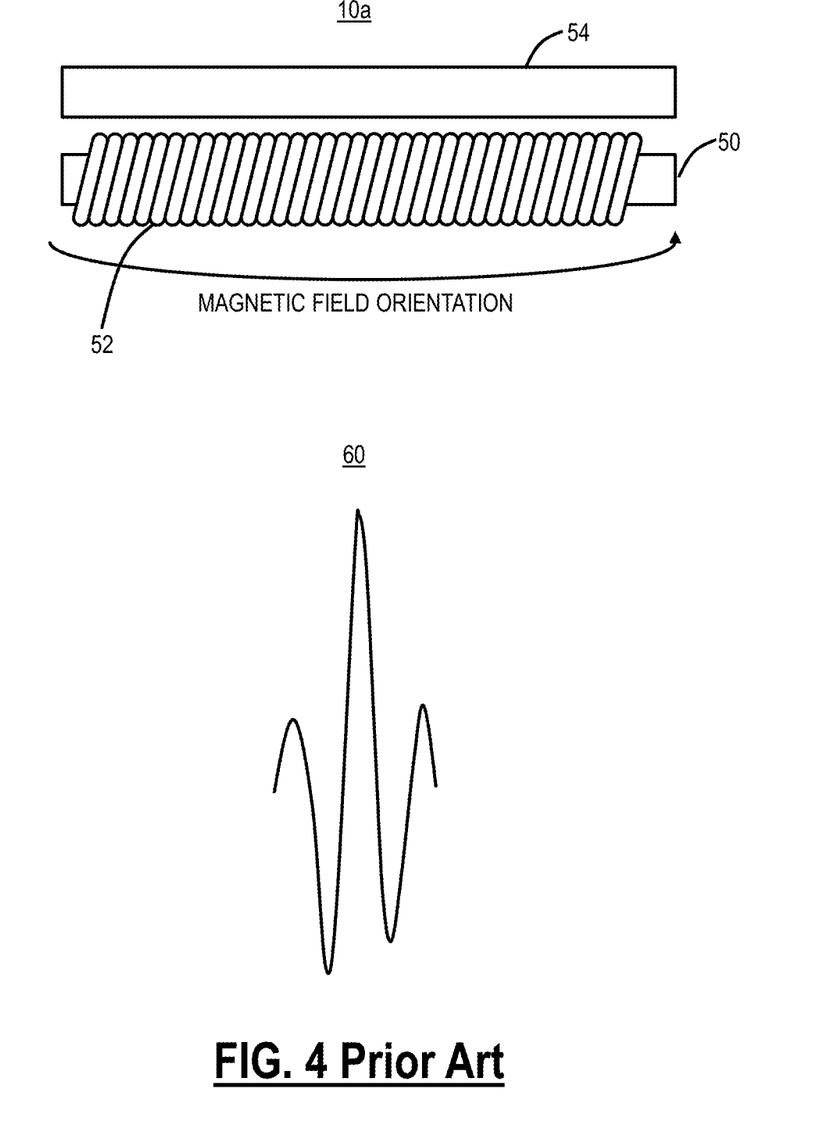
FIG. 4 is a block diagram of an implementation of a magnetostrictive transducer with a conventional coil arrangement.

Referring to FIG. 4, in a conventional embodiment, a block diagram illustrates an implementation of a magnetostrictive transducer 10a with a conventional coil arrangement. Similar to the magnetostrictive transducer 10 in FIG. 1, the magnetostrictive transducer 10a includes a magnetostrictive rod 50 with a coil 52 wrapped around and a proximate biasing magnet 54. From a terminology perspective, the wire or conductor which constitutes the coil 52 is called the winding. The hole in the center of the coil 52 is called the core area or magnetic axis. Each loop of wire is called a turn. In windings in which the turns touch, the wire must be insulated with a coating of nonconductive insulation such as plastic or enamel to prevent the current from passing between the wire turns. The winding is often wrapped around a coil form made of plastic or other material to hold it in place. The ends of the wire are brought out and attached to an external circuit.

Here, in the conventional coil arrangement, the coil 52, which carries the applied current, is wrapped tightly around the magnetostrictive rod 50. That is, the coil 52 has substantially no open space between turns, where the magnetostrictive rod 50 is exposed. The magnetic field orientation is shown in FIG. 4 extended from a left side of the magnetostrictive rod 50 to the right side. Finally, an ultrasonic wave 60 is shown illustrating an exemplary waveform produced by the magnetostrictive transducer 10a. Again, the magnetostrictive transducer 10a is typically limited to producing the ultrasonic wave 60 with frequencies below 200 kHz and has a very narrow bandwidth or range of operating frequencies (e.g., 120 kHz transducer will not operate around 110 kHz or 130 kHz drive frequency).

Magnetostrictive ultrasonic transducers are ideal candidates for metal wire waveguide applications because they can be welded directly to the waveguide, resulting in superior mechanical coupling compared to piezoelectric transducers. However, magnetostrictive transducers operate at much lower frequencies than piezoelectrics (up to about 200 kHz for magnetostrictive transducers versus 0.5-100 MHz common to piezoelectric transducers), resulting in lower possible signal resolution. The frequency of a magnetostrictive transducer is dependent on its length (shorter length, resulting in higher frequency), but reducing length also reduces signal strength.

Figure 5:
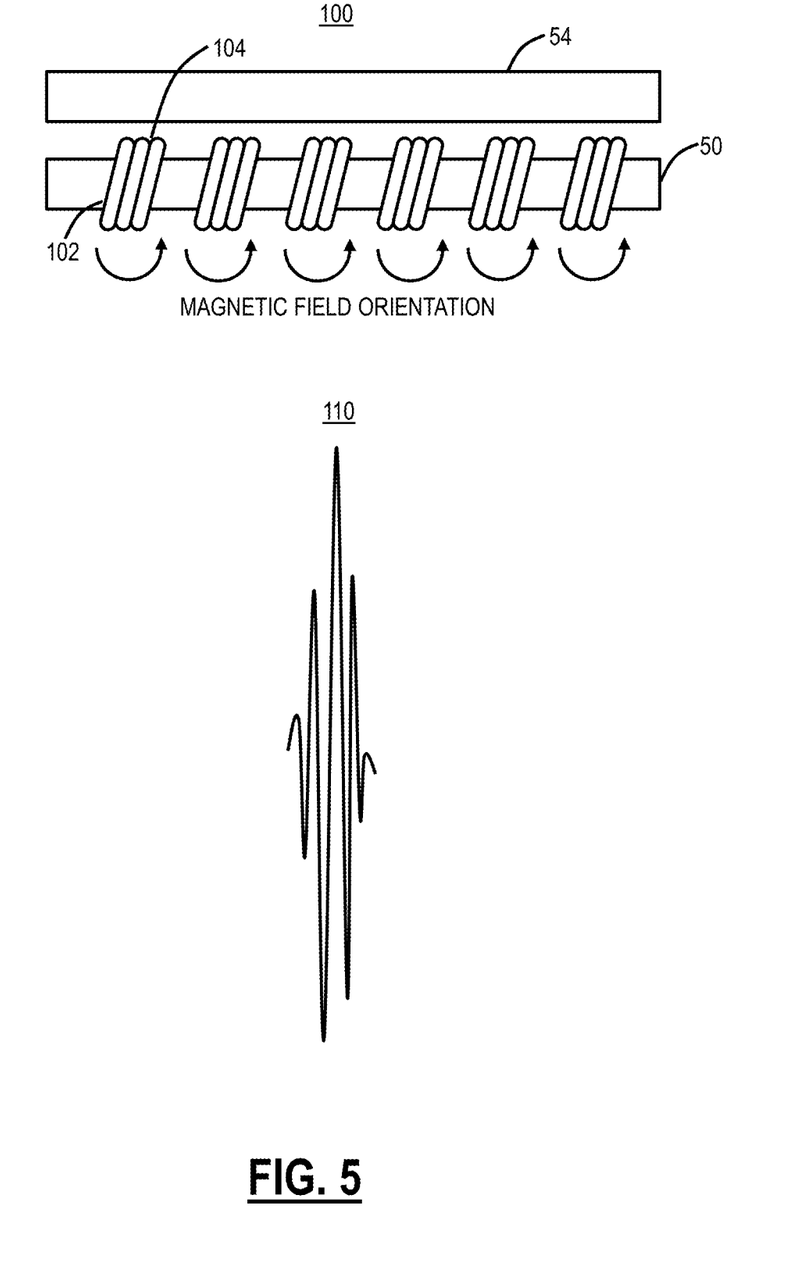
FIG. 5 is a block diagram of a high frequency magnetostrictive transducer with an advanced coil arrangement in an exemplary embodiment.

Referring to FIG. 5, in an exemplary embodiment, a block diagram illustrates a high frequency magnetostrictive transducer 100 with an advanced coil arrangement. The high frequency magnetostrictive transducer 100 includes the magnetostrictive rod 50 and the proximate biasing magnet 54 along with a coil 102 in the advanced coil arrangement. The high frequency magnetostrictive transducer 100 the magnetostrictive rod 50 or wire inserted co-axially into a driving coil 102. The coil is of the solenoidal type, but broken into many small coil segments 104. The small coil segments 104 are electrically connected in series, and may be wound in alternating directions or in a uniform direction (the uniform direction is shown in FIG. 5). The frequency of operation is controlled by both the length of the small coil segments 104 and the material of the magnetostrictive rod 50 or wire (which has a natural frequency of operation). The small coil segments 104 allow the magnetostrictive rod 50 or wire material to be driven at higher harmonics, resulting in the higher frequency. The waves generated by each coil segment 104 interfere constructively with each other, resulting in greater signal strength, as shown by the magnetic field orientation. The biasing magnet 54 must be used to precondition the magnetostrictive material of the magnetostrictive rod 50 or wire.

FIG. 5 also includes an ultrasonic wave 110 shown illustrating an exemplary waveform produced by the high frequency magnetostrictive transducer 100. As compared to the ultrasonic wave 60, the ultrasonic wave 110 is at a much higher frequency. The new design results in the high frequency magnetostrictive transducer 100 operating into the MHz range, without loss of signal strength. This is achieved through the use of a new coil design, with the small coil segments 104. This design retains the beneficial aspects of the magnetostrictive design, while reducing its primary drawback, lower frequency operation. Again, typical frequencies range from about 20 kilohertz to several hundred kilohertz in the magnetostrictive transducer 10, 10a; whereas the new design of the high frequency magnetostrictive transducer 100 has been observed to operate at up to approximately 2 megahertz with increased bandwidth, or operating range (e.g., a prototype coil operates between ~1 and 3 MHz). The frequency is dependent on both the coil design and the magnetostrictive material.

In an exemplary embodiment, the high frequency magnetostrictive transducer 100 includes a magnetostrictive rod 50 or wire inserted co-axially into a driving coil 102, wherein the driving coil 102 includes a coil arrangement with a plurality of small coil segments 104 along the magnetostrictive rod 50 or wire; wherein frequency operation of the high frequency magnetostrictive transducer 100 is controlled by a length of the small coil segments 104 and a material type of the magnetostrictive rod 50 or wire. The peak frequency operation of the high frequency magnetostrictive transducer 100 has been demonstrated up to approximately 2 MHz. The demonstrated high frequency magnetostrictive transducer 100 can operate between approximately 1 MHz and 3 MHz. Each of the small coil segments 104 can be spaced apart from adjacent small coil segments 104 with open space on the magnetostrictive rod 50 or wire therebetween. The plurality of small coil segments 104 can each form a magnetic field orientation that collectively constructively interfere with one another, resulting in greater signal strength. Optionally, the plurality of small coil segments 104 can be each wound in a uniform direction. Alternatively, the plurality of small coil segments 104 can be each wound in alternating directions. The plurality of small coil segments 104 allow the magnetostrictive rod 50 or wire to be driven at higher harmonics, resulting in higher frequency operation. In another exemplary embodiment, a high frequency magnetostrictive transducer method includes inserting a magnetostrictive rod 50 or wire co-axially into a driving coil 102, wherein the driving coil 102 include a coil arrangement with a plurality of small coil segments 104 along the magnetostrictive rod 50 or wire; wherein frequency operation of the high frequency magnetostrictive transducer 100 is controlled by a length of the small coil segments 104 and a material type of the magnetostrictive rod 50 or wire.

The spacing between each small coil segment 104 and the length of each small coil segment 104 are preferably optimized for the desired frequency operation. Preferably, the length of each small segment 104 is approximately equal to the spacing of each segment. As used herein, "approximately" preferably means having no measurable difference in the resulting output of the magnetostritive transducer from that of the resulting output when length of each small segment 104 is equal to the spacing of each segment, more preferably within 10%. In a preferred embodiment, the spacing between each small coil segment 104 and the length of each small coil segment 104 is optimized using the equation $L = c/2 \cdot f$, where c is sound velocity in the magnetostrictive material, which is a constant, f is frequency, and L is length of each small coil segment 104, as well as the length of the spacing between the small coil segments. As the small coil segment gets shorter, the frequency increases but the signal strength decreases. By utilizing multiple coils with gaps between each segment, the signal strength can be restored. This is due to constructive interference of the waves. If the spacing does not match the coil length, this effect does not occur. Adding more segments increases the signal strength, but also increases the number of wave cycles generated. This has the effect of increasing, overall, the length of the waveform. Preferably, more than two small coil segments 104 are used, more preferably 3 to 5 small coil segments.

Preferably, an A.C. signal is passed through each small coil segment 104, preferably a sinusoidal as the electromagnetic field charges and discharges in a logarithmic way. In a preferred embodiment, the A.C. signal passed through each small coil segment 104 includes a pulse, more preferably a plurality of sinusoidal pulses, preferably producing pulses of sinusoidal waves having a frequency greater than 1 MHz, more preferably between 1 MHz and 3 Mhz. In alternate embodiments, Gaussian pulses or time reversed signals may also be used as desired.Referring to FIG. 6, in an exemplary embodiment, a block diagram illustrates another high frequency magnetostrictive transducer 100a with an advanced coil arrangement. The high frequency magnetostrictive transducer 100a is similar to the high frequency magnetostrictive transducer 100a with the small coil segments 104 electrically connected in series in alternating directions. Here, the magnetic field orientation includes destructive interference. Mechanical wave interference is still constructive.

Figure 7:
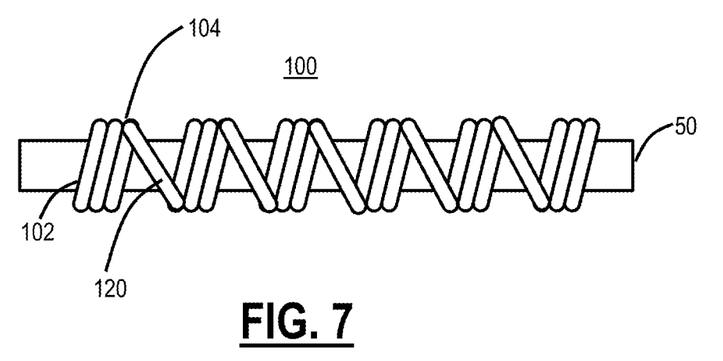
FIG. 7 is a block diagram of the high frequency magnetostrictive transducer of FIG. 5 showing a rear portion and associated interconnections between the small coil segments.

Referring to FIG. 7, in an exemplary embodiment, a block diagram illustrates the high frequency magnetostrictive transducer 100 showing a rear portion and associated interconnections between the small coil segments 104. Here, each small coil segment 104 is connected by a wire portion 120 that extends across the magnetostrictive rod 50 or wire material, rather than being wrapped around.

Figure 8:
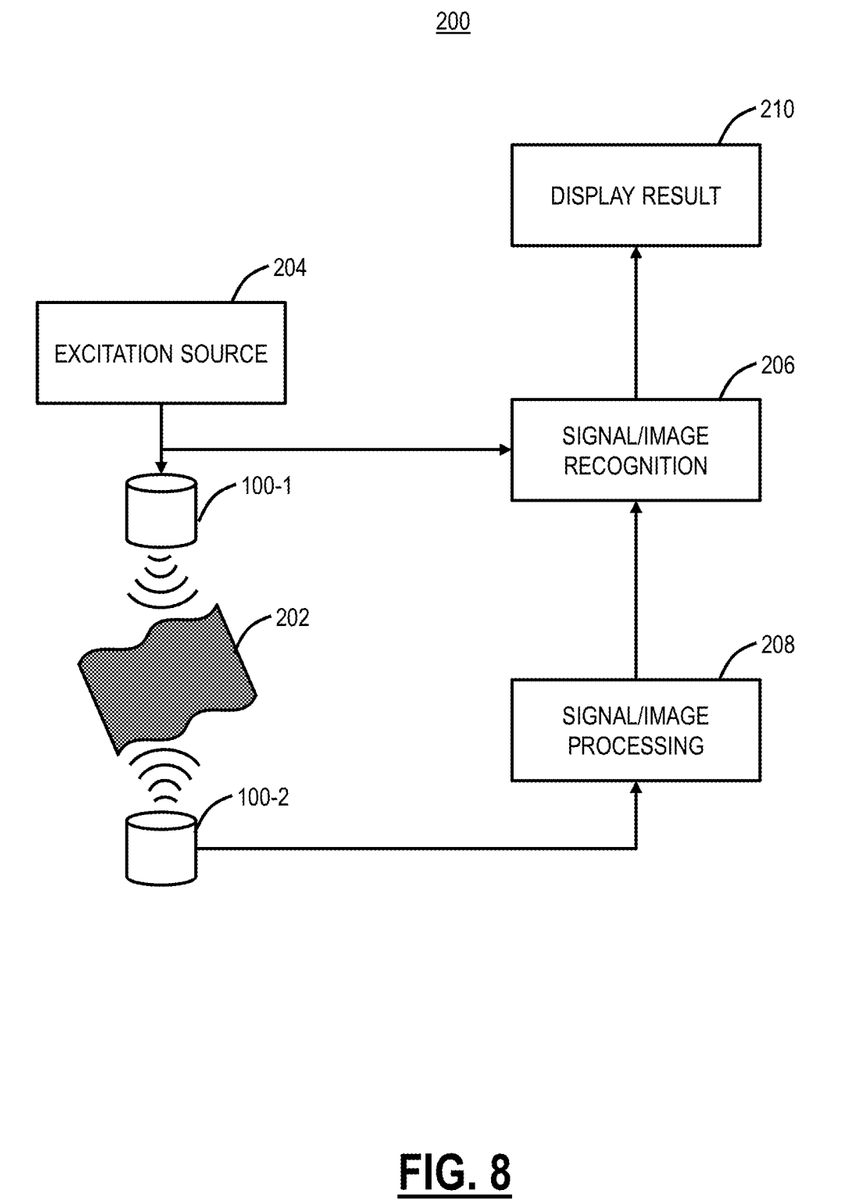
FIG. 8 is a block diagram of an ultrasonic transducer system using high frequency magnetostrictive transducers.

Referring to FIG. 8, in an exemplary embodiment, a block diagram illustrates an ultrasonic transducer system 200 using high frequency magnetostrictive transducers 100-1, 100-2. The ultrasonic transducer system 200 is used for non-destructive evaluation to scan objects and identify defects in a sample 202. The ultrasonic transducer system 200 includes an input high frequency magnetostrictive transducer 100-1 to provide ultrasonic waves to the sample 202 and a measurement high frequency magnetostrictive transducer 100-2 for measurement therefrom. The input high frequency magnetostrictive transducer 100-1 is coupled to an excitation source 204 which is also coupled to a signal/image recognition block 206. The measurement high frequency magnetostrictive transducer 100-2 is coupled to a signal/image processing block 208 which is also coupled to the signal/image recognition block 206. The signal/image recognition block 206 is coupled to a display result block 210 which is configured to provide user output based on a test of the sample 202.

In operation, the excitation source 204 is used to drive the input high frequency magnetostrictive transducer 100-1 to evaluate the sample 202. The measurement high frequency magnetostrictive transducer 100-2 is used to detect the high frequency sound waves from the input high frequency magnetostrictive transducer 100-1 off the sample 202. The blocks 206, 208 are used to process and evaluate the results from the high frequency magnetostrictive transducers 100-1, 100-2.

Figure 9:
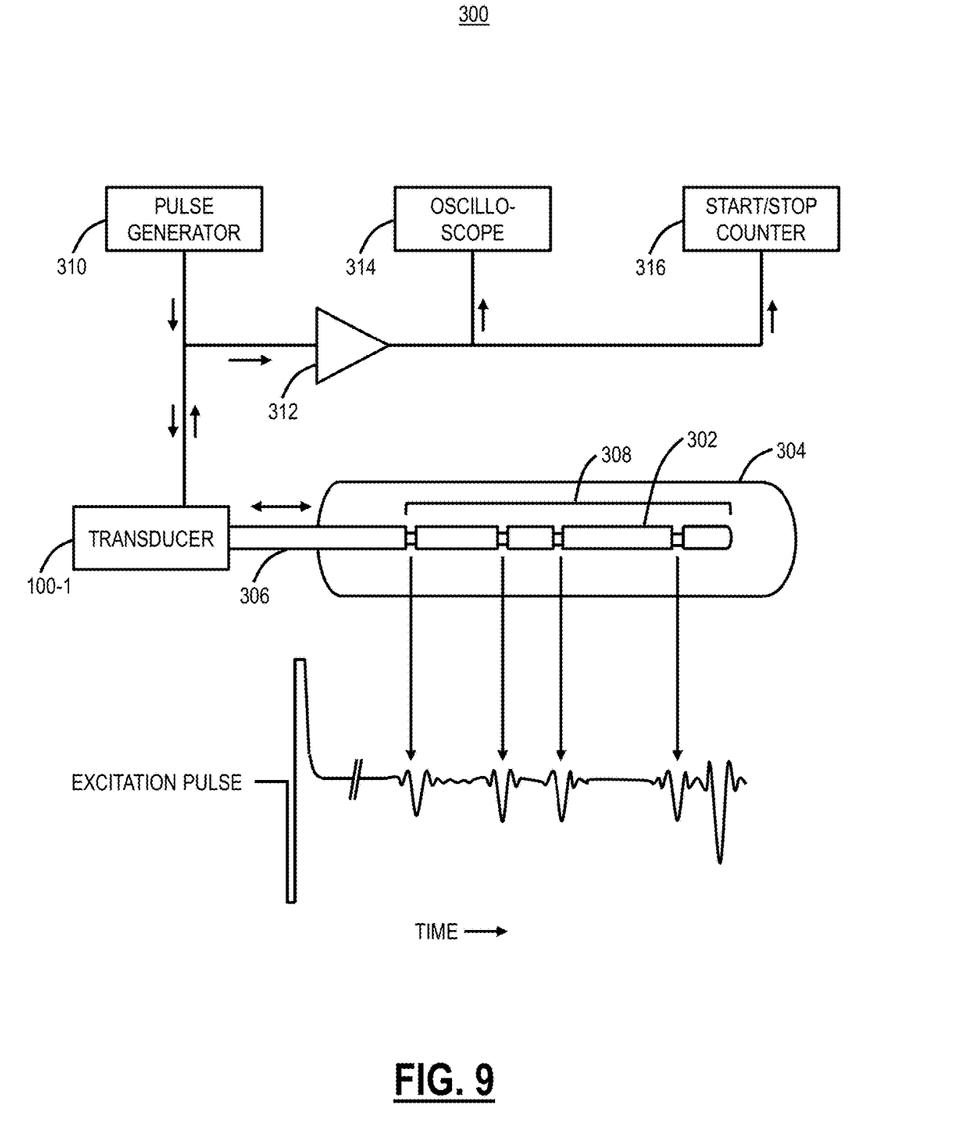
FIG. 9 is a block diagram of an ultrasonic sensor system using the high frequency magnetostrictive transducer.

Referring to FIG. 9, in an exemplary embodiment, a block diagram illustrates an ultrasound based sensor system 300 using the high frequency magnetostrictive transducer 100-1 to evaluate a rod 302 in a sheath 304. For example, the rod 302 can be a segmented metallic rod, and the high frequency magnetostrictive transducer 100-1 advantageously provides better resilience than the piezoelectric transducer 20 while having similar frequency performance. The ultrasonic transducer system 300 can include the input high frequency magnetostrictive transducer 100-1 coupled to a waveguide 306 and a sensor 308 within the sheath 304 along the rod 302. The input high frequency magnetostrictive transducer 100-1 can be coupled to a pulse generator 310 for input. For output, the input high frequency magnetostrictive transducer 100-1 is coupled to an amplifier 312 configured to amplify an output signal and display on an oscilloscope 314 and a start/stop counter 316.

In the ultrasonic systems 200, 300, the high frequency magnetostrictive transducers 100 can be used to generate high frequency sound waves, for non-destructive evaluation to scan objects and identify defects. The high frequency magnetostrictive transducers 100 can also be used as a core technology of various sensor systems for measuring a wide variety of parameters. Additional applications are also contemplated for the high frequency magnetostrictive transducers 100 such as, without limitation, ultrasonic cleaning, ultrasonic welding, material property testing (density, Young's Modulus, etc.), and the like.

In the ultrasonic transducer systems 200, 300, the high frequency magnetostrictive transducers 100 can be incorporated into enhanced ultrasonic sensors in Materials and Test Reactors (MTRs), commercial and naval fleets, and spent fuel casks. For example, the high frequency magnetostrictive transducers 100 can be incorporated into thermometers (high temperature applications >1800° C.; high radiation conditions), liquid level sensors (for post-Fukushima accident tolerant instrumentation in steam generators and pressurizers in Pressurized Water Reactors (PWRs) and in the Reactor Pressure Vessel for Boiling Water Reactors (BWRs)), flow meters, displacement sensors, structural monitoring systems, and the like. Magnetostrictive transducers are used in many applications as sensors and actuators, with the frequency commonly being a limiting factor. The new design could be used to expand the range of applications these transducers are used for.

Figure 6:
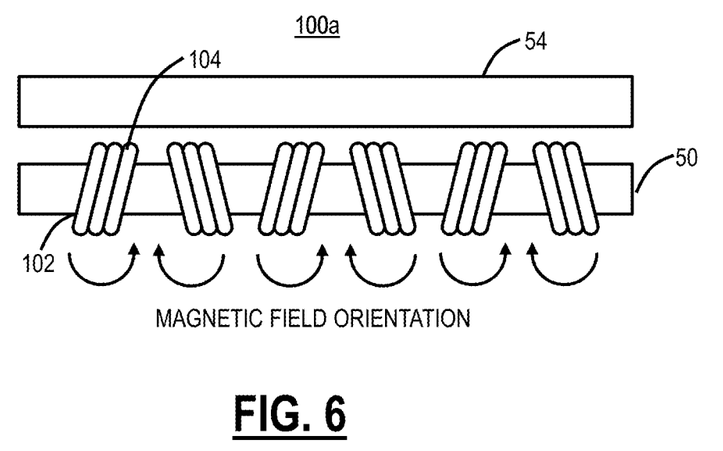
FIG. 6 is a block diagram of another high frequency magnetostrictive transducer with an advanced coil arrangement.

In an exemplary embodiment, a high frequency magnetostrictive transducer system 200, 300 includes one or more high frequency magnetostrictive transducers 100 comprising a magnetostrictive rod 50 or wire inserted co-axially into a driving coil 102, for example as shown in FIG. 6 and FIG. 7, wherein the driving coil 102 includes a coil arrangement with a plurality of small coil segments 104 along the magnetostrictive rod 50 or wire, and wherein frequency operation of the high frequency magnetostrictive transducer 100 is controlled by a length of the small coil segments 104 and a material type of the magnetostrictive 50 rod or wire; a source (e.g., the excitation source 204 or the pulse generator 310) configured to drive the one or more high frequency magnetostrictive transducers 100; and a detection device (e.g., the blocks 206, 208, 210 or the oscilloscope 314) coupled to the one or more high frequency magnetostrictive transducers 100. The high frequency magnetostrictive transducer 100 operates at a peak center frequency of approximately 2 MHz, and the high frequency magnetostrictive transducer 100 can operate between approximately 1 MHz and 3 MHz. Each of the small coil segments 104 can be spaced apart from adjacent small coil segments 104 with open space on the magnetostrictive rod 50 or wire therebetween. The plurality of small coil segments each form a magnetic field orientation that collectively constructively interfere with one another, resulting in greater signal strength.

Figure 10:
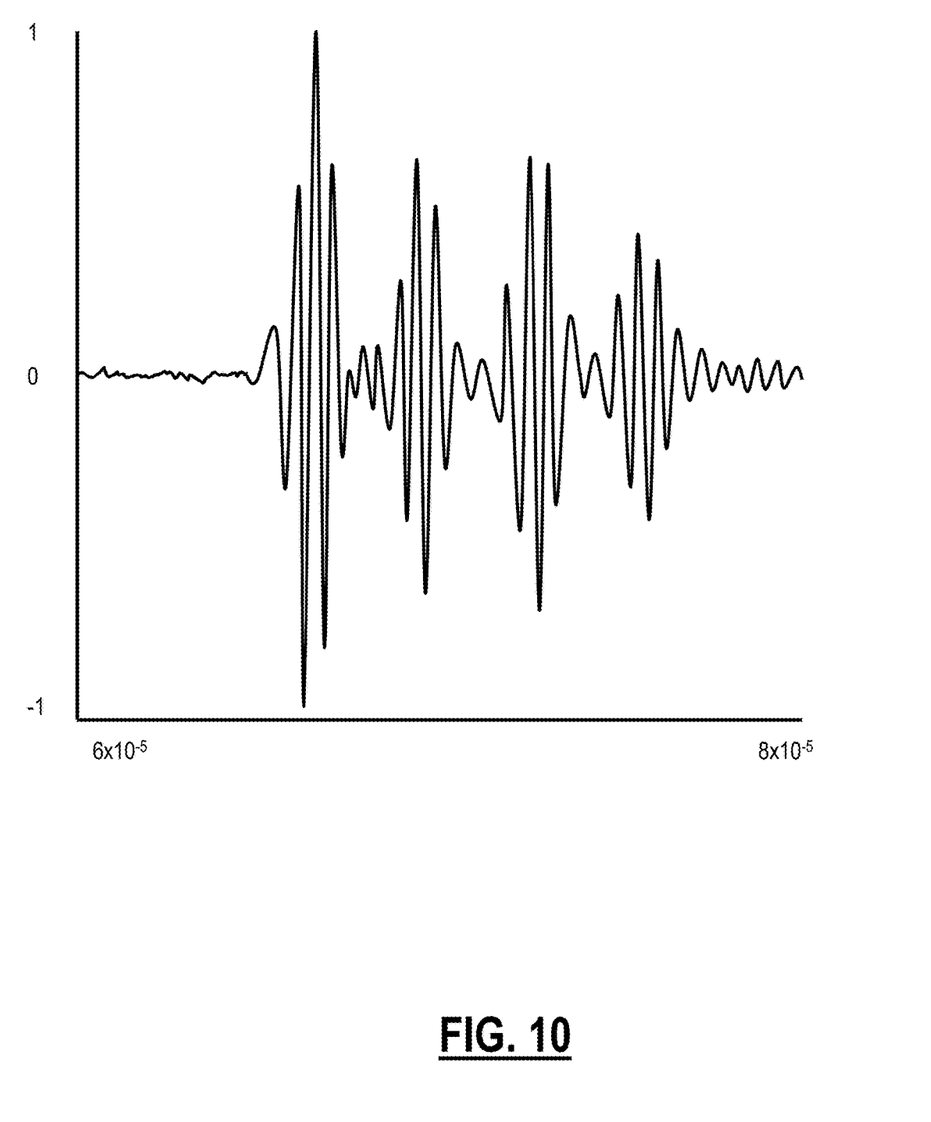
FIG. 10 is a graph of an evaluation of the high frequency magnetostrictive transducer showing an ability to clearly distinguish reflectors spaced at 1 cm.

Referring to FIG. 10, in an exemplary embodiment, a graph illustrates an evaluation of the high frequency magnetostrictive transducer 100 showing an ability to clearly distinguish reflectors spaced at 1 cm. Note, this is a factor of 3 improvement over the traditional coil arrangement in the magnetostrictive transducer 10 of similar total size. Test results, for the high frequency magnetostrictive transducer 100, indicate significant increase in operating frequency and improvement in signal strength. Coils operating at 488 kHz, 1098 kHz, 1220 kHz, and 1830 kHz were demonstrated.

Figure 11:
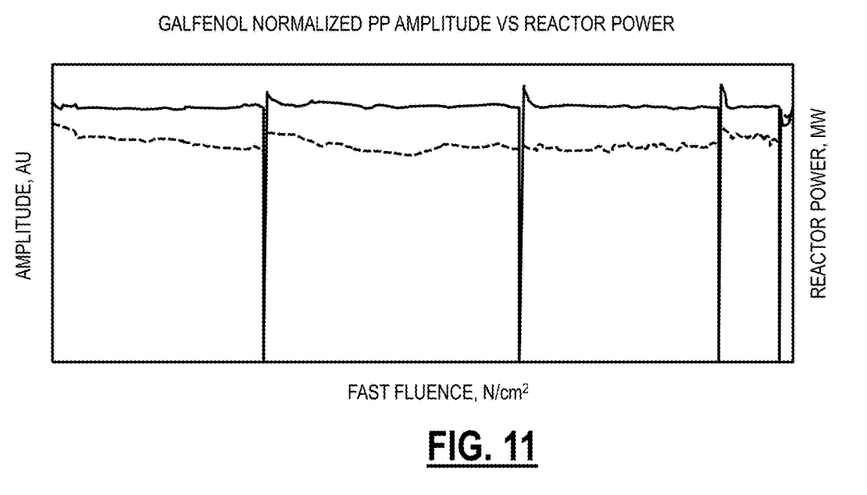
FIGS. 11 and 12 are graphs of results of irradiation tests of candidate materials that could be used in the high frequency magnetostrictive transducer.
Figure 12:
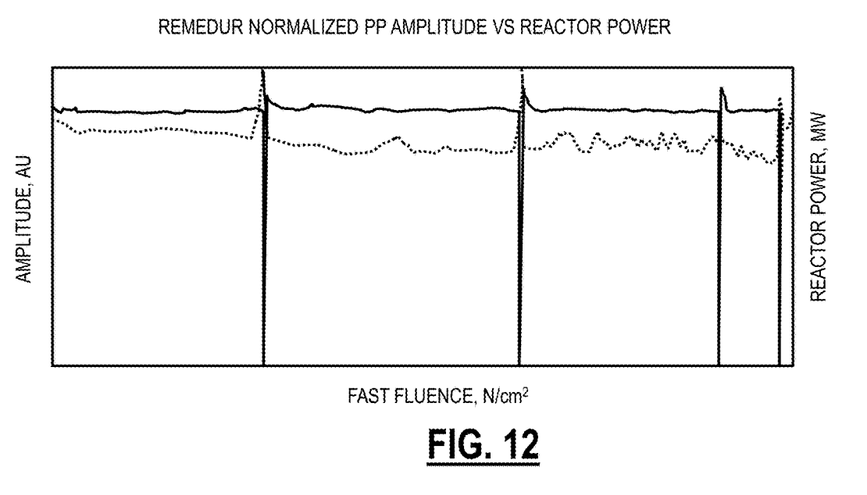

Referring to FIGS. 11 and 12, in an exemplary embodiment, graphs illustrate results of irradiation tests of materials that could be used in the high frequency magnetostrictive transducer 100. Specifically, FIG. 11 is a graph of radiation effects on Galfenol (Galfenol is an alloy of iron and gallium and is a product of Etrema Products, Inc.) magnetostriction, which appear negligible after irradiation to $1.5*10^{20}$ n/cm². FIG. 12 is a graph of radiation effects on Remendur magnetostriction, which are minor after irradiation to $1.5*10^{20}$ n/cm². Temperature effects appear dominant.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. A high frequency magnetostrictive transducer comprising:

a magnetostrictive rod or wire inserted co-axially into a driving coil, wherein the driving coil comprises a coil arrangement with a plurality of small coil segments electrically connected in series along the magnetostrictive rod or wire;

wherein an operating frequency of the high frequency magnetostrictive transducer is controlled by a length of the small coil segments and a material type of the magnetostrictive rod or wire; and wherein the length of each small coil segment and a spacing between each of the small coil segments are approximately defined by the equation $L=c/2 \cdot f$, where c is a sound velocity in the magnetostrictive rod or wire, f is the operating frequency, and L is the length of each small coil segment or the spacing between the small coil segments.

2. The high frequency magnetostrictive transducer of claim 1, wherein a peak center frequency of the high frequency magnetostrictive transducer is up to approximately 2 MHz.

3. The high frequency magnetostrictive transducer of claim 1, wherein a bandwidth or an operating frequency range of the high frequency magnetostrictive transducer is between approximately 1 MHz and 3 MHz.

4. The high frequency magnetostrictive transducer of claim 1, wherein each of the small coil segments is spaced apart from adjacent small coil segments with open space on the magnetostrictive rod or wire therebetween.

5. The high frequency magnetostrictive transducer of claim 1, wherein the plurality of small coil segments each form a magnetic field. orientation that collectively constructively interfere with one another, resulting in greater signal strength.

6. The high frequency magnetostrictive transducer of claim 1, wherein the plurality of small coil segments are each wound in a uniform direction.

7. The high frequency magnetostrictive transducer of claim 1, wherein the plurality of small coil segments are each wound in alternatingdirections.

8. The high frequency magnetostrictive transducer of claim 1, wherein the plurality of small coil segments are configured to allow the magnetostrictive rod or wire to be driven at a frequency between approximately 1 Mhz and 3 Mhz with greater than 50% signal amplitude.

9. The high frequency ma.gnetostrictive transducer of claim 1, wherein the plurality of small coil segments comprises more than two small coil segments.

10. The high frequency magnetostrictive transducer of claim 1, wherein the length of each small coil segment and the spacing between each small coil segments is approximately equal.

11. A high frequency magnetostrictive transducer system comprising:

one or more high frequency magnetostrictive transducers comprising a magnetostrictive rod or wire inserted co-axially into a driving coil, wherein the driving coil comprises a coil arrangement with a plurality of small coil segments electrically connected in series along the magnetostrictive rod or wire, and wherein an operating frequency of the high frequency magnetostrictive transducer is controlled by a length of the small coil segments and a material type of the magnetostrictive rod or wire, and wherein the length of each small coil segment and a spacing between each small coil segments is approximately defined by the equation $L=c/2 \cdot f$, where c is a sound velocity in the magnetostrictive rod or wire, f is the operating frequency, and L is the length of each small coil segment or spacing between the small coil segments;

a source configured to drive the one or more high frequency magnetostrictive transducers; and a detection device coupled to the one or more high frequency magnetostrictive transducers.

12. The high frequency magnetostrictive transducer system of claim 11, wherein a peak center frequency of the high frequency magnetostrictive transducer is up to approximately 2 MHz, and wherein an operating frequency range of the high frequency magnetostrictive transducer is between approximately 1 MHz and 3 MHz.

13. The high frequency magnetostrictive transducer system of claim 11, wherein each of the small coil segments is spaced apart from adjacent small coil segments with open space on the magnetostrictive rod or wire therebetween.

14. The high frequency magnetostrictive transducer system of claim 11, wherein the plurality of small coil segments each form a magnetic field orientation that collectively constructively interfere with one another, resulting in greater signal strength.

15. The high frequency magnetostrictive transducer of claim 11, wherein the plurality of small coil segments are configured to allow the magnetostrictive rod or wire to be driven at a frequency between approximately 1 Mhz and 3 Mhz with greater than 50% signal amplitude.

16. The high frequency magnetostrictive transducer of claim 11, wherein the plurality of small coil segments comprises more than two small coil segments.

17. The high frequency magnetostrictive transducer of claim 11, wherein the length of each small coil segment and the spacing between each small coil segments is approximately equal.

18. The high frequency magnetostrictive transducer of claim 11, wherein the source produces a plurality of sinusoidal pulses; and each produced sinusoidal pulse having a frequency greater than 1 MHz and matching the operating frequency of the high frequency magnetostrictive transducer.

* * * * *